(12) United States Patent  
Paskal et al.

(10) Patent No.: US 7,179,436 B2
(45) Date of Patent: Feb. 20, 2007

(54) STERILIZATION SYSTEM AND METHOD

(75) Inventors: Darren T. Paskal, 1135 N. Mansfield Ave., 4th Floor, Los Angeles, CA (US) 90038; Gregory L. Noss, 4001 S. Dacatur Blvd., Suite 37-527, Las Vegas, NV (US) 89103; William P. Conley, Calabasas, CA (US); Rodger D. Thomason, Santa Monica, CA (US)

(73) Assignees: Darren T. Paskal, Los Angeles, CA (US); Gregory L. Noss, Los Angeles, CA (US)

( * ) Notice: Subject to any disclaimer, the term of this patent is extended or adjusted under 35 U.S.C. 154(b) by 0 days.

(21) Appl. No.: 10/860,922

(22) Filed: Jun. 4, 2004

(65) Prior Publication Data

US 2004/0258559 A1 Dec. 23, 2004

Related U.S. Application Data

(60) Provisional application No. 60/476,516, filed on Jun. 5, 2003.

(51) Int. Cl.
*A61L 2/07* (2006.01)

(52) U.S. Cl. ............ 422/295; 422/292; 422/297; 422/26

(58) Field of Classification Search ........... 422/26, 422/299, 292, 295, 297
See application file for complete search history.

(56) References Cited

U.S. PATENT DOCUMENTS

| | | | |
|---|---|---|---|
| 3,361,517 A | 1/1968 | Skaller | |
| 3,961,893 A | 6/1976 | Russell et al. | 21/95 |
| 4,105,407 A | 8/1978 | Sanderson | 21/56 |
| 4,238,447 A | 12/1980 | Wolff | 422/26 |
| 4,562,047 A | 12/1985 | Sestak et al. | 422/300 |
| 4,663,122 A | 5/1987 | Sparks | 422/26 |
| 4,748,003 A | 5/1988 | Riley | 422/112 |
| 4,783,321 A * | 11/1988 | Spence | 422/300 |
| 4,865,814 A | 9/1989 | Childress | 422/116 |
| 4,944,919 A | 7/1990 | Powell | 422/26 |
| 5,029,252 A | 7/1991 | Ameseder | 250/455.1 |
| 5,145,642 A | 9/1992 | Feathers, III et al. | 422/26 |
| 5,213,776 A * | 5/1993 | Maniero et al. | 422/303 |
| 5,253,927 A | 10/1993 | Erickson | 300/2 |
| 5,277,875 A | 1/1994 | Albright et al. | 422/109 |
| 5,340,200 A | 8/1994 | Erickson | 300/2 |
| 5,735,061 A * | 4/1998 | Lawrence | 34/493 |
| 5,919,416 A | 7/1999 | Auner | 422/26 |
| D413,986 S | 9/1999 | Lin | D24/217 |
| 6,039,926 A * | 3/2000 | Goldman | 422/116 |
| 6,058,247 A | 5/2000 | Lahey et al. | 392/399 |
| 2004/0126274 A1* | 7/2004 | Song et al. | 422/26 |

FOREIGN PATENT DOCUMENTS

| | | |
|---|---|---|
| EP | 0337793 | 10/1989 |
| WO | WO 92/03170 | 3/1992 |
| WO | WO 02/068003 | 2/2002 |

* cited by examiner

*Primary Examiner*—Krisanne Jastrzab
*Assistant Examiner*—Sean E Conley
(74) *Attorney, Agent, or Firm*—Donn K. Harms

(57) ABSTRACT

Exemplary embodiments may include a sanitizing system and method including a chamber, a wet and dry heating system adjacent to the chamber, and a filtered air system to reduce the contaminants entering the system and to provide positive pressure to the chamber to reduce the likelihood of contaminants entering the system.

25 Claims, 5 Drawing Sheets

STERILIZATION SYSTEM AND METHOD

CROSS REFERENCE TO RELATED APPLICATIONS

This application claims priority to Provisional Patent Application Ser. No. 60/476,516, entitled "LOW PRESSURE HOME SANITIZING AUTOCLAVE WITH CONTINUOUS MOIST OR DRY AIRFLOW", filed Jun. 5, 2003, and is incorporated herein in its entirety for all purposes.

BACKGROUND

Several conventional approaches for sanitizing surfaces of personal hygiene articles and the like may be known. However, all known conventional apparatuses and methods have one or more disadvantages.

One conventional approach may be to soak the articles in a chemical disinfectant. Unfortunately, chemical disinfectants may not reach all of the surfaces of some articles, such as the surfaces between tightly compacted bristles found in many toothbrushes. This approach may be problematic especially if the exposure of the articles to the chemical disinfectant is brief. In addition, such chemical disinfectants may be relatively costly and may have to be frequently resupplied. Accordingly, use of chemical disinfectants may not be entirely effective.

Another approach may be to sanitize personal hygiene articles using microwave energy. So-called microwave disinfecting may be problematic because of the electrical arcing that may occur with metal used in the articles, such as the metal cleats sometimes used to anchor bristles in a toothbrush head. Additionally, most households may not be equipped with a microwave apparatus outside of the kitchen. Therefore, use of this approach may be inconvenient for many household users.

Still another approach to sanitize articles may be to expose the articles to ultraviolet light. However effective, ultraviolet light equipment may also be expensive and may require regular maintenance by a skilled technician. Also, ultraviolet light may not always reach all surfaces of the articles, such as between the tightly compacted bristles found in many toothbrushes. Further, ultraviolet light may degrade some thermoplastic materials. Moreover, repeated exposure of a user to ultraviolet light may present safety concerns, such as accidental vision damage, among others.

Some current systems may also allow contaminants to enter the system during and/or after the sanitization process. This may reverse the effects of the sanitization process, thereby making the sanitization process less effective.

As noted above, some apparatuses and methods have disadvantages that make their use unappealing and/or disadvantageous to most household users. Accordingly, there is a need for a compact, inexpensive, safe, easy, ready-to-use, and effective apparatus that sanitizes articles, including personal hygiene articles and other items such as toothbrushes, after each use by subjecting the articles to moist heat, dry heat, and/or filtered air. Furthermore, what is needed is a system and method that may keep items sanitized and/or reduce contaminants that contact the items before, during and/or after the sanitization takes place.

SUMMARY

Exemplary embodiments provided herein may include an apparatus, including a heating system, an article-holding system, and a method for sanitizing articles, including personal hygiene articles, such as toothbrushes, without the need for solvents, radiation, ozone, ionization, chlorine, alcohol, bleach, or other chemicals.

Further provided may be a sanitary environment for storing articles, including personal hygiene articles such as toothbrushes, after sanitizing them, and to provide such an environment wherein there is no need to handle the articles after they have been subjected to a sanitizing operation until their next use.

Further embodiments may provide a compact, inexpensive, energy-efficient apparatus to for sanitizing articles, including personal hygiene articles such as toothbrushes, and for storing the articles after the sanitizing operation until their next use, utilizing wet heat, dry heat and/or filtered air and/or a pressurized system.

DETAILED DESCRIPTION

The detailed description set forth below in connection with the appended drawings is intended as a description of exemplary embodiments and is not intended to represent the only forms in which the embodiments may be constructed and/or utilized. The description sets forth the functions and the sequence of steps for constructing and operating illustrated embodiments. However, it is to be understood that the same or equivalent functions and sequences may be accomplished by different embodiments that are also intended to be encompassed within the spirit and scope of this disclosure.

Figure 1:
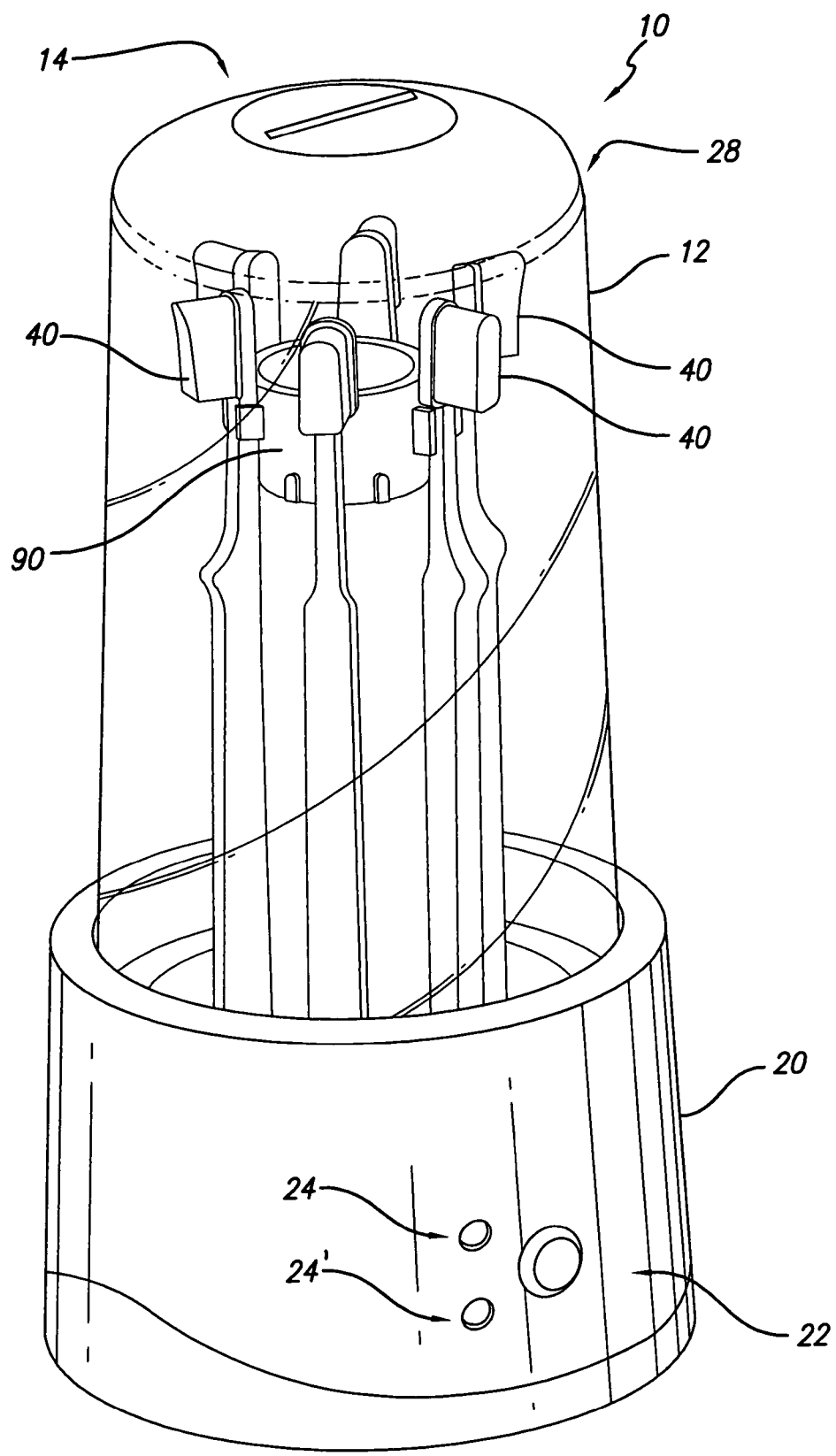
FIG. 1 is a perspective view of a sanitizing system according to one exemplary embodiment.

A sanitizing system according to an exemplary embodiment is shown in FIG. 1, generally at 10. System 10 may include a cover 12, which may be configured to couple to a housing 20 to form a chamber 28 therebetween. Chamber 28 may surround and/or enclose items 40 as well as item support system 90. Cover 12 may include a vent 14 which may allow air and/or liquid to exit the system.

Cover 12 may be selectively, removably secured to housing 20, and extends generally vertically upwardly from housing 20, and its interior space defines an enclosure or chamber 28 for enclosing articles to be sanitized. Cover 12 may secure to housing via a screw configuration, an interference fit, and/or a snap lock-type configuration, among others as desired. Furthermore, although cover 12 is shown as a generally cylindrical shape, it will be appreciated that other shapes and configurations can be used, as desired.

Housing 20 may include an actuator 22 which, when actuated, may start and/or stop a sanitizing process, as desired. Furthermore housing 20 may include indicators 24 and 24', which may indicate whether a sanitizing cycle is started, currently happening, and/or ended, as desired. It will be appreciated that other numbers of indicators 24 may be utilized, as desired.

It will be appreciated that although cover 12 is shown generally as a cylindrical shape, other shapes and configurations may be utilized, as desired. Furthermore, although vent 14 is shown as a slot or generally rectangular opening, other configurations may be utilized, as desired. Similarly, although housing 20 and cover 12 are shown as generally circular and cylindrical, other shapes may be utilized including square, rectangular, domed, or other configurations, as desired. Yet further, even though system 10 is shown as being sized to house toothbrushes or smaller household items, it will be appreciated that the system may be sized for sanitizing other items, including dishes, dental appliances, or other items that a user may wish to sanitize, as desired.

Figure 2A:
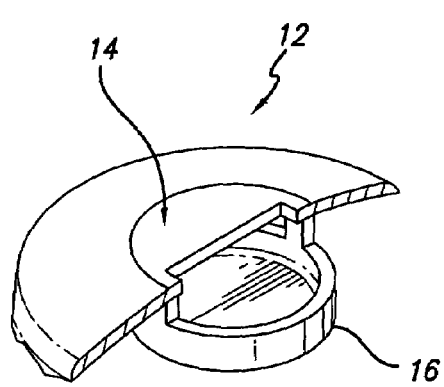
FIG. 2A is a sectional view along line 2A—2A of the embodiment of FIG. 2.
Figure 2:
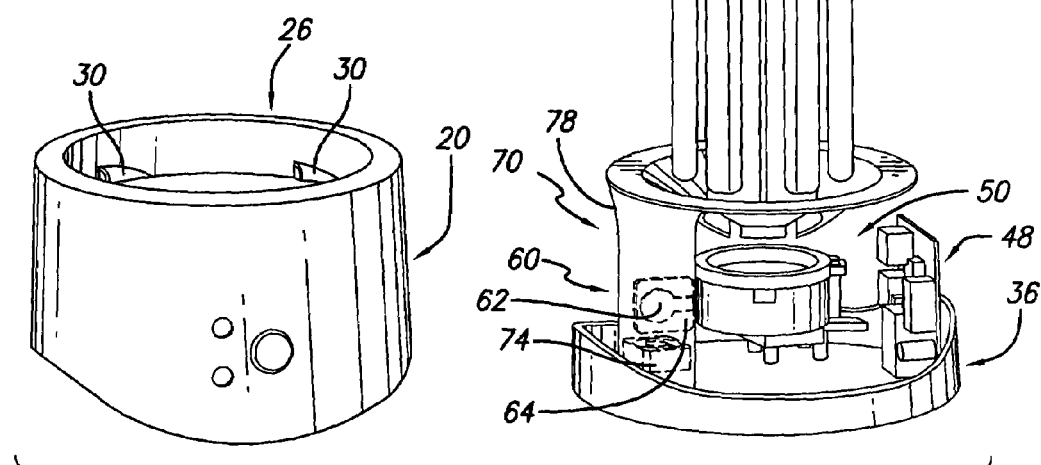
FIG. 2 is an exploded view of the embodiment of FIG. 1.

FIG. 2 is an exploded view of the embodiment of sanitizing system 10 as shown in FIG. 1. Again, system 10 may include a cover 12 which may include a vent 14. Furthermore system 10 may include an item support system 90 which may be configured to support items to be sanitized 40. Furthermore, item support system 90 may be configured to rest within base 36 and/or couple to it via numerous ways, including, but not limited to, an interference fit, friction fit, or rotational fit, among others, as desired. In this manner, item support system 90 may rest and/or couple to housing 20 to support items to be sanitized 40.

System 10 may also include a base 36 which may be configured to couple to housing 20. It will be appreciated that although housing 20 and base 36 are shown as two pieces, they may be one piece of molded plastic, as desired. Base 36 and housing 20 may be configured to enclose other components of the system including a control system 48. Control system 48 may be configured to control the overall operation of the system, as desired.

Further enclosed in system 10 may be a wet heat system 50 which may be configured to provide wet heat to chamber 28, such as steam, to sanitize the items 40. Housing 20 may include a reservoir 26 which may hold a sanitizing liquid, water, or other materials and or media that may be utilized in the sanitization process, as desired. Wet heat system 50 may be configured to heat up the liquid in reservoir 26 to create steam to sanitize the items in chamber 28.

System 10 may further include a dry heat system 60 as well as a filtered air system 70. Filtered air system 70 may include a fan, 74 such that air and/or other gases may be circulated throughout the chamber 28. Furthermore, it will be appreciated that with fan 74 running, chamber 28 is pressurized thus reducing the amount and/or likelihood of contaminants entering the system and/or chamber 28. Dry heat system 60 may sanitize and/or sterilize the items 40 with dry heat. Furthermore, dry heat system 60 may evaporate and/or remove liquids from the items 40, such that microbial growth may be reduced.

Filtered air system 70 may further include a duct 78 which may include duct outlets 30 within chamber 28. With this configuration, fan 74 will move air through duct 78 and into chamber 28 via duct outlets 30. Although two duct outlets 30 have been shown, it will be appreciated that other numbers and configurations for duct outlets may be utilized, as desired. With this generally closed configuration, contaminants may be eliminated and/or reduced in the air entering the system, as well as contaminants entering the system via vent 14.

Dry heat system 60 may include a dry heating structure 62 as well as an enhancer 64. Dry heating structure 62 may be an electrical heater such as a common "lollipops-type" electric resistive heater, however other heating structures and configurations may be utilized, without straying from this concept. Dry heat system 60 may further include an enhancer 64, which may be configured to dissipate heat from dry heating structure 62 such that more heat may be applied to the system, so that dry heating structure 62 may not overheat. This configuration may allow dry heating structure 62 to last longer without the need to have it replaced or lengthen the time the dry heating structure would operate, thereby reducing the cost of maintaining the system.

Cover 12, housing 20, base 36, and other portions of system 10 may be made of a polymeric material that may be either thermally set, thermoplastically formed, or injection molded, or other materials, as desired. Furthermore, a plastic treated with an antibacterial agent or an inorganic antimicrobial ceramic mix plastic may be utilized to further reduce contaminants in the system. However, it will be appreciated that other materials and configurations may be utilized, as desired. These components may be opaque, transparent, or translucent, as desired. Furthermore, the exterior surfaces may include designs that would appeal to users, including children. Also, materials such as stainless steel and glass may be utilized for a more robust system, such as, but not limited to, one used in a hospital or other commercial application, as desired.

Item support system 90 may be configured to support dental appliances, such as, but not limited to, toothbrushes, retainers, and guides, as well as may others, as desired. Furthermore, item support system 90 may be configured to support baby appliances such as, but not limited to, bottles, pacifiers, toys, eating utensils, plates, bibs, hair fasteners, among many others, as desired. Also, item support system 90 may be configured to support a wide variety of household items such as, but not limited to, dishes, silverware, cleaning devices, among many others, as desired. Furthermore, item support system may be configured to support piercing equipment and jewelry, and the like, as desired. Also, item support system 90 may be configured to support a wide variety of personal items such as, but not limited to, combs, brushes, tweezers, nail and hair clippers, and the like, as desired.

Furthermore, multiple item support systems may be utilized in combination together, such that different types of items may be sanitized together. Also, different item support systems may be configured to couple to each other to increase the flexibility of the system, as desired. It will be appreciated that the many different item support systems may be configured to be removable and interchangeable within the system to make the system very versatile. Also, the items support system may be individually packaged such that it may be discarded after one use. This configuration may be utilized in hotels and the like, such that a patron or user may use the item support system once and throw it away to further limit microbial or other contamination.

FIG. 2A is a cut away view along lines 2A—2A of FIG. 2, of cover 12. As shown in FIG. 2 and FIG. 2A, cover 12 may include a vent 14 as well as a containment structure 16. Containment structure 16 may be configured to contain contaminants such as, but not limited to, water or other liquids spilled or placed on the top of the system, such that with the positive pressure generated by fan 74, contaminants will be reduced and/or less likely to enter the system via vent 14. Containment structure 16 and vent 14 may create a tortuous path such that contaminants that may enter the system via vent 14 may not contaminate the sanitized items. With this configuration, liquids or other things inadvertently dropped on the system may be less likely to contaminate the items 40 or the chamber 28. It will be appreciated that other configurations may be utilized for vent 14 and containment structure 16 without straying from the concepts disclosed herein.

It will be appreciated that although containment structure 16 is shown generally as a cylinder, other configurations may be utilized, depending upon the overall system design and the items to be sanitized, as desired.

Figure 3:
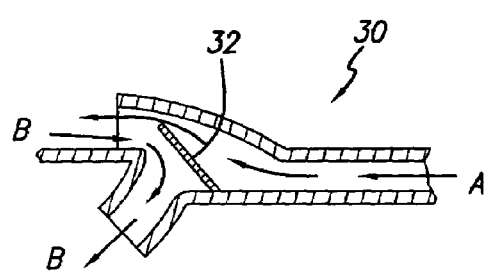
FIG. 3 is a cut-away view of a duct outlet according to an exemplary embodiment.

FIG. 3 shows a cut away view of a duct outlet 30, according to one exemplary embodiment, generally at 30. Duct outlet 30 may include a flap 32, which may be configured to open when air is exiting the duct outlet 30 along the arrows labeled A. As shown in FIGS. 2 and 3, flap 32 may then be biased back toward the source of the air such that when liquids or other items enter the duct outlet as shown by the arrows labeled B, they will not enter the duct outlet 30 or duct 78. With this configuration, contaminants are less likely to enter the filtered air system 70, duct 78 and duct outlet 30. It will be appreciated that although this particular configuration is shown for a duct outlet 30, many other configurations may be utilized that will allow air to pass along the line of arrows labeled A while not allowing contaminants, and/or liquids, and/or other items to enter the duct and pass into the filtered air system 70 or other parts of the system.

With this configuration, wet heat, dry heat, filtered air, and positive pressure may be utilized to sanitize the items 40 during a cycle. Furthermore, the cycle and/or process and/or method may include maintaining a positive pressure in chamber 28 until a user would like to use the items 40, such that they may be maintained in a sanitized state between the sanitization cycle and use.

Figure 4:
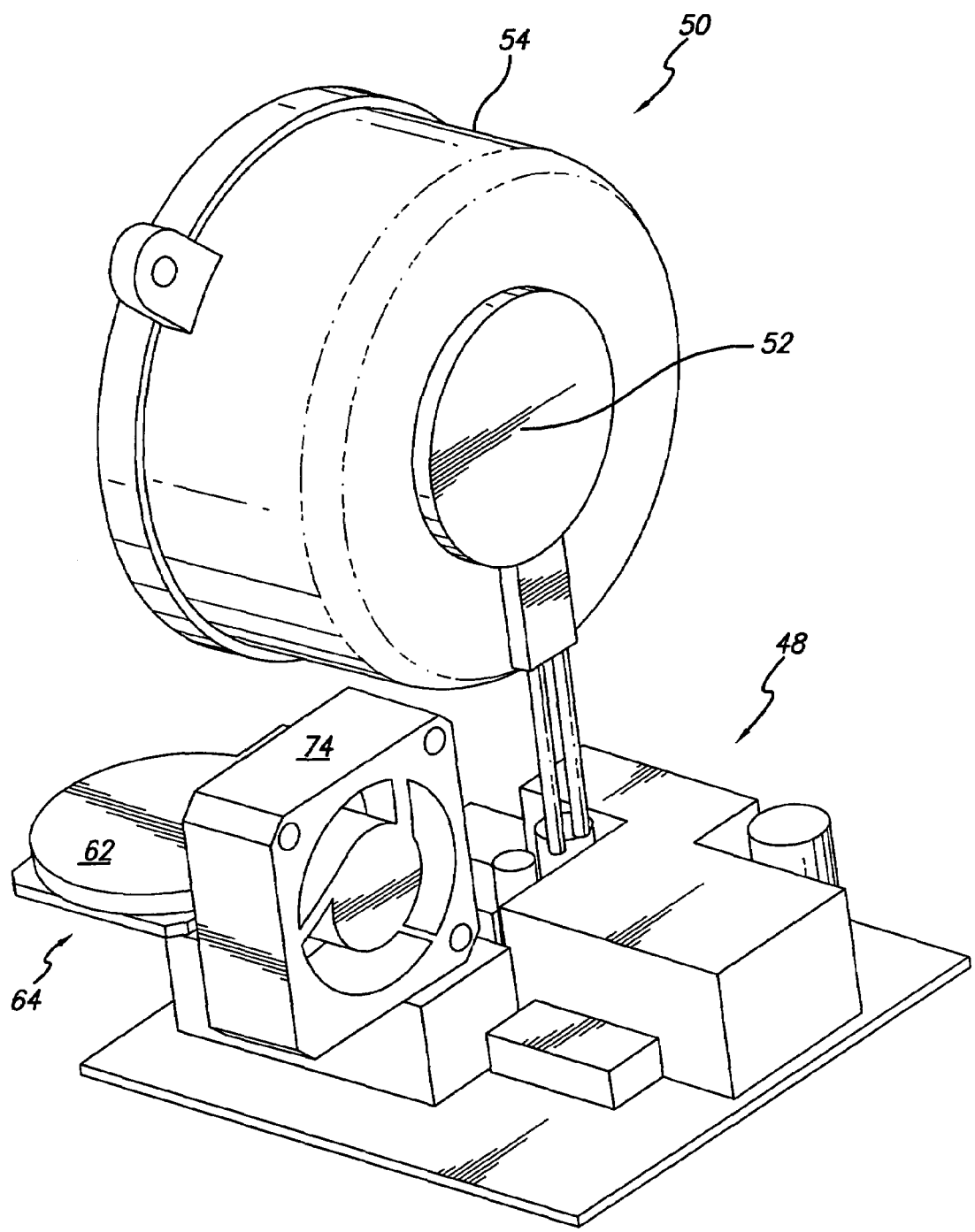
FIG. 4 is a more detailed perspective view of the heating systems and control systems of exemplary embodiments.

FIG. 4 is a more detailed perspective view of the heating systems and control systems of an exemplary embodiment. Wet heat system 50 may include a wet heating structure 52 and a container 54. Wet heating structure 52 may be a common "lollipop-type" electric resistive heating element, however it will be appreciated that many other types of heating structures may be utilized for this purpose, without straying from the concepts disclosed herein.

Wet heat system 50 may further include a container 54 which may be configured to hold a sanitizing liquid and/or may be configured to transfer heat from wet heating structure 52 to reservoir 26 (not shown). The sanitizing liquid may be water that is heated to create saturated steam to sanitize the articles in the system, however, it will be appreciated that other sanitizing liquids may be utilized, as desired. With this configuration, heat may be transferred to a liquid, such as a sanitizer, water, or other liquid or solid within the system such that it may evaporate and/or create steam to sanitize the items 40 (also not shown).

Also shown is a control system 48 which may control the overall operation of the elements and structures of the system as well as the processes and methods disclosed herein. Also included in this figure are fan 74 as well as dry heat structure 62 and enhancer 64, as described above. It will be appreciated that fan 74 may blow across dry heat element 62 to provide dry heat to the system. If dry heat element 62 is not activated, fan 74 may still provide positive pressure to chamber 28 (not shown), such that positive pressure will be maintained in the chamber and system such that contaminants may be less likely to enter the system.

During a wet sanitizing cycle, liquid reservoir 26 (not shown) is filled with a sanitizing liquid and wet heat system 50 may be activated to convert the sanitizing liquid to saturated steam to sanitize the articles within the system. A typical cycle would include a wet sanitizing system, a dry sanitizing system, and/or filtered air pressurization to reduce microbial growth and reduce contaminants in the system.

During the drying cycle, dry heat system 60 may be activated and fan 74 may force hot, dry air into the container to further sanitize the articles therein. Fan 74 may operate during the entire sanitizing cycle and may continue to operate to ensure that the chamber is pressurized such that few, if any, contaminating articles enter through vent 14 or in any other manner, into the system.

Both wet and dry heating systems may include a self-regulating heating element that may improve the control and operation of the system. Furthermore, the use of two heating systems may increase the efficiency, control and durability of the system.

Figure 5:
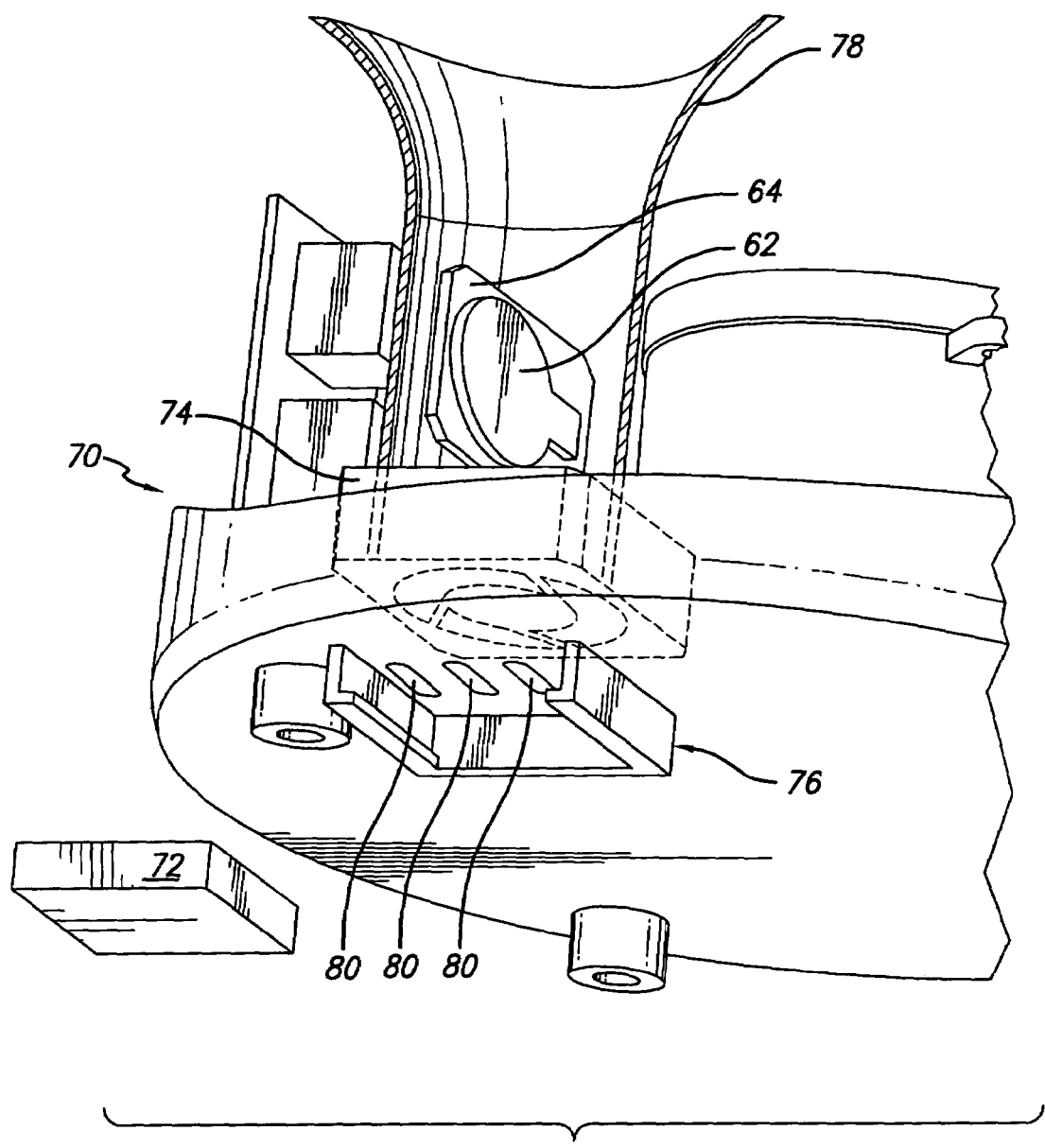
FIG. 5 is a more detailed perspective view of the filtered air system according to an exemplary embodiment.

FIG. 5 is a more detailed perspective view of the filtered air system, according to an exemplary embodiment. Filtered air system 70 may include a filter 72 which may be configured to fit within a filter housing 76, to reduce particulate, contaminants, and other things from entering the system via the openings 80. Filter 72 may be a hepa-type filter, carbon filter, paper filter, cloth filter, activated charcoal filter, or other filter that may be utilized for this purpose. It will be appreciated that although filter 72 is shown as generally square or rectangular, other shapes, configurations, and/or sizes may be utilized, as desired. Similarly, filter housing 76 may be configured in a different manner depending on the size, shape and type of filter 72 utilized for this system.

Filtered air system 70 may further include a fan 74 which may be configured to draw air from outside of the system through openings 80 and into duct 78. It will be appreciated that the air entering the system will be filtered and may be less likely to contain contaminants that would enter the system. The air may then pass though duct 78 and through duct outlets 30 (not shown) and enter the chamber 38 (also not shown). Fan 74 may run continuously, such that a positive pressure is maintained in the system. This method and configuration may reduce contaminants entering the system and maintain the sanitized items 40 (not shown) in a sanitized state, until the user removes cover 12 (not shown) and uses the items. Furthermore dry heating structure 62 and enhancer 64 may be disposed within duct 78 such that dry heat would be imparted to the chamber 28 (not shown) via the air moved by fan 74.

Figure 6:
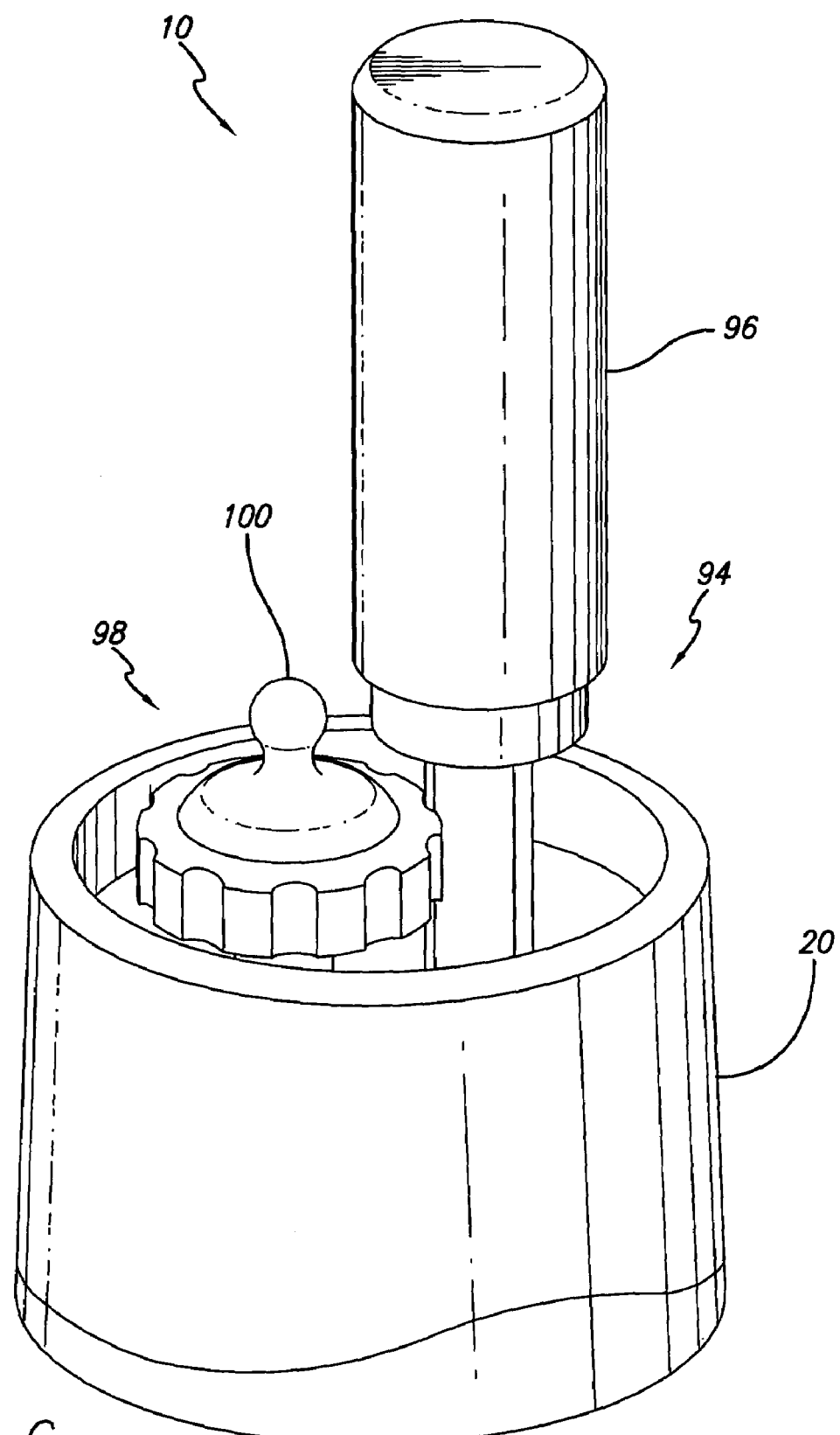
FIG. 6 is a perspective view of a bottle support system according to one exemplary embodiment.

FIG. 6 shows a bottle support system 94 according to one exemplary embodiment. Bottle support system 94 may couple to housing 20 or other parts of the system as described above. Bottle support system 94 may be configured to support a bottle 96 as well as a top 98 and nipple 100. With this configuration a baby's bottle may be supported within the system via bottle support system 94. It will be appreciated that although item support system 90 and bottle support system 94 are shown, many different configurations for a support system may be utilized, as desired. It will be appreciated that another support system may include the structures to support many baby bottles as well as children's toys, pacifiers, and the like. Furthermore support systems may include structures that would support dishes, dental appliances, tools, surgical instruments, jewelry, piercing items, and many other items that a user wishes to sanitize, as desired. Similarly, the size of the system may be varied to accommodate different items to be sanitized.

Therefore with a method of sanitization that includes wet heat, dry heat, filtered air, and positive pressure, contaminants may be more likely to be reduced and items to be sanitized may have less contaminants and/or germs than other systems and methods. It will be appreciated that this method and system may be utilized for many different types of sanitization, as desired. Furthermore systems may include the use of ozone and/or ultraviolet light to further enhance the sanitization and operation of this system. Furthermore with this method and process, recontamination of the items will be less likely to occur via contaminants entering the system via air vent 14.

Another method may include providing a chamber and maintaining positive pressure in the chamber to reduce the contaminants contacting the items. This method and system may be enhanced by filtering the air entering the chamber. This embodiment may provide an inexpensive way to reduce contaminants. This may be utilized at night with a user placing items in the chamber before sleeping to reduce the likelihood of contaminants contacting the items overnight.

Referring generally to all figures, the advantages of this system may include small size and increased life of heating elements, as there are separate wet and dry heating systems. Furthermore, the configuration with the filter 72 and the fan 74, and vent 14, may ensure that the amounts of contaminating materials are reduced in the system. Furthermore, the operation of the fan 74 during the entire sanitization cycle may ensure that the chamber 28 remains pressurized, further reducing contaminates entering the system through vent 14 in the top of cover 12 or in any other manner.

Furthermore, this system may allow sanitization of many household items, whether they are made of plastic or metal or any other material. Other systems utilizing a microwave to heat up a sanitizing liquid to convert it to saturated steam, may not be able to sanitize any object with metal in them as this may interfere with the operation of the microwave. Furthermore, this present system may be very small, takes up little space, and may be inexpensive to manufacture and distribute such that it will be readily usable by many people. The design of this system may also be attractive in appearance, which may lead consumers to more readily purchase one or more systems.

Typically, a person may fill the reservoir 26 with a sanitizing liquid to a certain level, then place the items 40 on an item support system 90, and place them in the system 10. Then the cover 12 may be coupled to the housing 20 to create a generally airtight chamber 26 therein. The system 10 may be then activated and the wet sanitizing system 50 may be activated to begin wet sterilization. The wet sanitizing cycle may end when the sanitizing liquid has all been dispersed from the reservoir 26.

The fan 74 may run throughout the cycle and remain on until cover 12 is removed from the system 10 thereby ensuring the chamber 26 is pressurized and little or no contaminates enter the system. After the wet cycle, the dry heat system 60 may be activated and a dry cycle may begin that may heat up the chamber 26 using dry air to dry sanitize the articles within the system. However, it will be appreciated that other sequences and combinations of cycles may be performed to accomplish sanitization of the articles. The fan 74 may remain activated to ensure that few, if any, contaminates enter the system 10 after the sanitizing cycle is complete, or until the cover 12 is removed.

While the present invention has been described with regard to exemplary embodiments, it is recognized that additional variations may be devised and/or utilized without departing from the concepts disclosed herein. In closing, it is to be understood that the embodiments described herein are illustrative of the principles of exemplary embodiments. Other modifications that may be employed are within the scope of this disclosure. Thus, by way of example, but not of limitation, alternative configurations may be utilized in accordance with the teachings herein. Accordingly, the drawings and description are illustrative and not meant to be a limitation thereof.

What is claimed is:

1. A sanitizing system for sanitizing items, comprising:
    a sanitizing chamber formed by a base and a cover adapted for removable engagement to said base in an engaged position;
    a wet heat system in communication with said chamber configured to create steam in said chamber;
    a dry heat system adjacent to said chamber configured to provide a generally dry heat to said chamber;
    a filtered air system adjacent to said chamber configured to provide filtered air movement within said chamber and positive air pressure while said cover remains in said engaged position;
    a vent communicating through said cover, said vent providing means to continuously exhaust air under said positive pressure therethrough, in a continuous forced airstream, said forced airstream thereby providing continuous means to prevent contaminants from entering said sanitizing chamber through said vent;
    a containment structure positioned adjacent to said vent in an upper portion of said sanitizing chamber;
    said containment structure so positioned, defining a tortuous path for air exhausting under said positive pressure from said sanitizing chamber; and
    said containment structure so positioned providing means to catch and thereby prevent solid or liquid contaminants entering said sanitizing chamber through said vent from reaching said items or entering a lower portion of said sanitizing chamber.

2. The system of claim 1, further comprising an item support system configured to be selectively countable within said chamber, and configured to support items to be sanitized.

3. The system of claim 2 wherein said item support system is interchangeable.

4. The system of claim 1, wherein said chamber further comprises a reservoir configured to hold a liquid.

5. The system of claim 4, wherein said wet heat system comprises a wet heating structure configured to heat said reservoir and convert said liquid into steam.

6. The system of claim 1, further comprising a control system configured to control the overall operation of the sanitizing system.

7. The system of claim 1, wherein said dry heat system comprises:
    a dry heating structure configured to provide a generally dry heat to the system; and
    an enhancer adjacent to said dry heating structure, configured to dissipate heat from said dry heating structure.

8. The system of claim 1, wherein said filtered air system comprises:
    a fan configured to receive air from outside the system and propel the air into said chamber; and
    a filter configured to filter the air entering from outside the system to reduce the contaminants entering the-chamber.

9. A sanitizing system for sanitizing items, comprising:
    a sanitizing chamber formed between a base and a cover, comprising a reservoir configured to hold a liquid;
    a wet heat system adjacent to said chamber configured to evaporate said liquid;
    a dry heat system adjacent to said chamber configured to provide a generally dry heat to said chamber;

a filtered air system, comprising a fan, the filtered air system adjacent to said chamber configured to provide continuous filtered air movement and positive air pressure within the chamber;

a vent communicating through said cover, said vent providing means to continuously exhaust air having said positive air pressure therethrough, thereby providing means to reduce contaminants from entering said sanitizing chamber through said vent;

a containment structure positioned adjacent to said vent in an upper portion of said sanitizing chamber above a lower portion thereof;

said containment structure so positioned, thereby defining a tortuous path for air exhausting said vent under said positive pressure from said sanitizing chamber; and said containment structure having a surface adapted to catch said contaminants and thereby providing means to prevent solid or liquid contaminants from reaching said items or entering said lower portion of said sanitizing chamber below said containment structure; and an item support system configured to couple to said chamber, to support items to be sanitized.

10. The system of claim 9, wherein said filtered air system further comprises a filter configured to reduce the contaminants entering the sanitizing system.

11. The system of claim 9 wherein said item support system is interchangeable.

12. A sanitizing system for sanitizing items, comprising:
a base; a cover configured to removably couple to said base to form a chamber therebetween;
a wet heat system adjacent to said chamber configured to evaporate a liquid in said chamber;
a dry heat system adjacent to said chamber configured to provide a generally dry heat to said chamber; and
a filtered air system adjacent to said chamber configured to provide filtered air movement and positive air pressure within said chamber;
a vent communicating through said cover, said vent providing means to continuously exhaust air having said positive air pressure therethrough in a directional airstream exiting said chamber, thereby providing means to reduce contaminants from entering said chamber through said vent;
a containment structure positioned adjacent to said vent in an upper portion of said sanitizing chamber, above a lower portion thereof;
said containment structure so positioned, defining a tortuous path for air exhausting under said positive pressure from said sanitizing chamber; and
said containment structure so positioned providing means to catch and thereby prevent solid and liquid said contaminants from reaching said lower portion of said chamber.

13. The system of claim 12, wherein said chamber further comprises a reservoir configured to hold a liquid.

14. The system of claim 13, wherein said wet heat system comprises a wet heating structure configured to heat up said reservoir to evaporate said liquid.

15. The system of claim 12, further comprising an item support system to support items to be sanitized.

16. The system of claim 15 wherein said item support system is interchangeable.

17. The system of claim 15, wherein said item support system is configured to support dental appliances.

18. The system of claim 15, wherein said item support system is configured to support baby appliances.

19. The system of claim 15, wherein said item support system is configured to support household items.

20. The system of claim 12, further comprising a control system configured to control the overall operation of the sanitizing system.

21. The system of claim 12, wherein said dry heating system comprises:
a dry heating structure configured to provide a generally dry heat to the system; and
an enhancer adjacent to said dry heating structure, configured to dissipate heat from said dry heating structure.

22. The system of claim 12, wherein said filtered air system comprises:
a fan configured to receive air from outside the system and propel the air into said chamber; and
a filter configured to filter the air entering from outside the system to reduce the contaminants entering the chamber.

23. A sanitizing system for sanitizing items, comprising:
a base;
a cover configured to selectively couple to said base to form a sanitizing chamber therebetween, wherein said chamber includes a reservoir configured to hold a liquid;
a wet heat system comprising a wet heating structure, adjacent to said chamber configured to evaporate said liquid in said chamber;
a dry heat system comprising a dry heating structure, adjacent to said chamber configured to provide a generally dry heat to said chamber;
a filtered air system, comprising a fan and a filter, adjacent to said chamber configured to provide filtered air movement and positive air pressure within said chamber;
means to continuously vent said positive air pressure;
an item support system, configured to couple to said chamber, and configured to support items to be sanitized in a lower portion of said sanitizing chamber;
a containment structure positioned adjacent to said vent in an upper portion of said sanitizing chamber;
said containment structure so positioned, defining a tortuous path for air exhausting through said vent under said positive pressure from said sanitizing chamber;
said containment structure adapted to catch and contain contaminants entering said sanitizing chamber through said vent; and
said tortuous oath and said containment structure in combination thereby providing means to prevent liquid or solid said contaminants entering said upper portion of said sanitizing chamber from reaching said lower portion of said sanitizing chamber.

24. The system of claim 23, wherein said means to continuously vent said positive air pressure comprises a vent communicating through said cover, said vent providing means to continuously exhaust air having said positive air pressure therethrough, thereby providing means to reduce contaminants from entering said sanitizing chamber through said vent.

25. A sanitizing system for sanitizing items, comprising:
a base;
a cover having a sidewall and a top wall, and an aperture opposite said top wall, said aperture adapted for removable engagement to said base in an engaged position;
a sanitizing chamber defined by the area between said sidewall, said topwall, and said base, when said cover is in said engaged position;

means to support said items in said sanitizing chamber;

a wet heat system in communication with said sanitizing chamber configured to create steam in said sanitizing chamber for a first duration of time;

a dry heat system adjacent to said sanitizing chamber configured to provide a generally dry heat to said sanitizing chamber for a second duration of time;

means to communicate air into said sanitizing chamber thereby providing filtered air movement and positive air pressure in said sanitizing chamber, whereby air pressure in said sanitizing chamber is higher than air pressure exterior to said sanitizing chamber;

a vent communicating through said topwall, said vent providing means to continually exhaust said air under said positive pressure therethrough in a directional forced air stream;

a containment structure having a surface adapted to catch contaminants, positioned adjacent to said vent;

said containment structure so positioned, defining a tortuous oath for air exhausting from said sanitizing chamber and providing means to prevent solid or liquid of said contaminants from entering a lower portion of said sanitizing chamber below said containment structure; and said air exhausting said vent providing means to prevent said contaminants from entering into said sanitizing chamber through said vent.

* * * * *